(12) United States Patent
Nelson

(10) Patent No.: US 6,401,521 B1
(45) Date of Patent: Jun. 11, 2002

(54) METHOD OF PREVENTING MOVEMENT OF A PLANAR SENSOR ELEMENT PACKAGED IN A MAT SUPPORT

(75) Inventor: Charles Scott Nelson, Clio, MI (US)

(73) Assignee: Delphi Technologies, Inc., Troy, MI (US)

(*) Notice: Subject to any disclaimer, the term of this patent is extended or adjusted under 35 U.S.C. 154(b) by 0 days.

(21) Appl. No.: 09/417,794

(22) Filed: Oct. 27, 1999

(51) Int. Cl.⁷ .................. G01N 27/26; G01N 27/04
(52) U.S. Cl. ............ 73/31.05; 73/31.06; 73/23.31; 204/424; 204/426
(58) Field of Search ................ 73/23.2, 23.31, 73/31.05, 31.06, 866.5; 204/424, 426, 428

(56) References Cited

U.S. PATENT DOCUMENTS

| | | | | |
|---|---|---|---|---|
| 2,781,506 A | * | 2/1957 | Harrison | 73/31.05 |
| 4,786,399 A | * | 11/1988 | Wertheimer et al. | 204/424 |
| 5,039,972 A | * | 8/1991 | Kato et al. | 73/31.05 |
| 5,817,920 A | * | 10/1998 | Kuisell et al. | 73/23.31 |
| 5,935,399 A | * | 8/1999 | Tanaka et al. | 204/424 |
| 6,032,514 A | * | 3/2000 | Weyl et al. | 73/31.05 |
| 6,055,847 A | * | 5/2000 | Hafele et al. | 73/31.05 |
| 6,164,120 A | * | 12/2000 | Friese et al. | 73/23.2 |
| 6,266,997 B1 | * | 7/2001 | Nelson | 73/31.05 |

* cited by examiner

Primary Examiner—Hezron Williams
Assistant Examiner—Michael Cygan
(74) Attorney, Agent, or Firm—Vincent A. Cichosz

(57) ABSTRACT

In an exemplary embodiment, the planar sensing element (80) is secured by inclusion of a disk element support provided between the lower end of an inner shield and the lower shoulder of an outer shell for containing such shield, whereby the diameter of the disk element support is less than that of the shell to allow such disk element support to shift off-center. In a preferred embodiment, the planar sensing element is secured by incorporation of a mesh element support, comprising fine wire material and vermiculite filler.

33 Claims, 3 Drawing Sheets

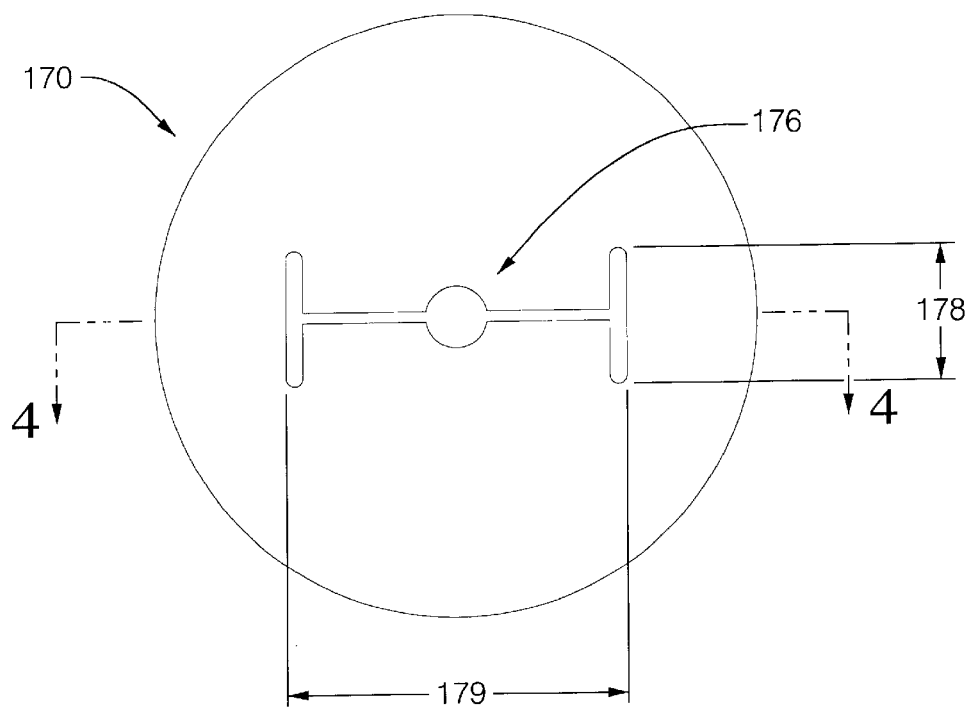
FIG. 3
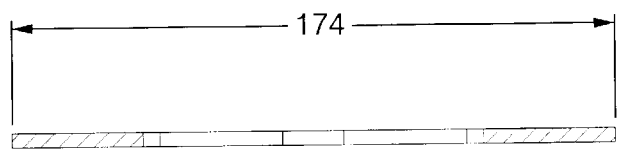
FIG. 4
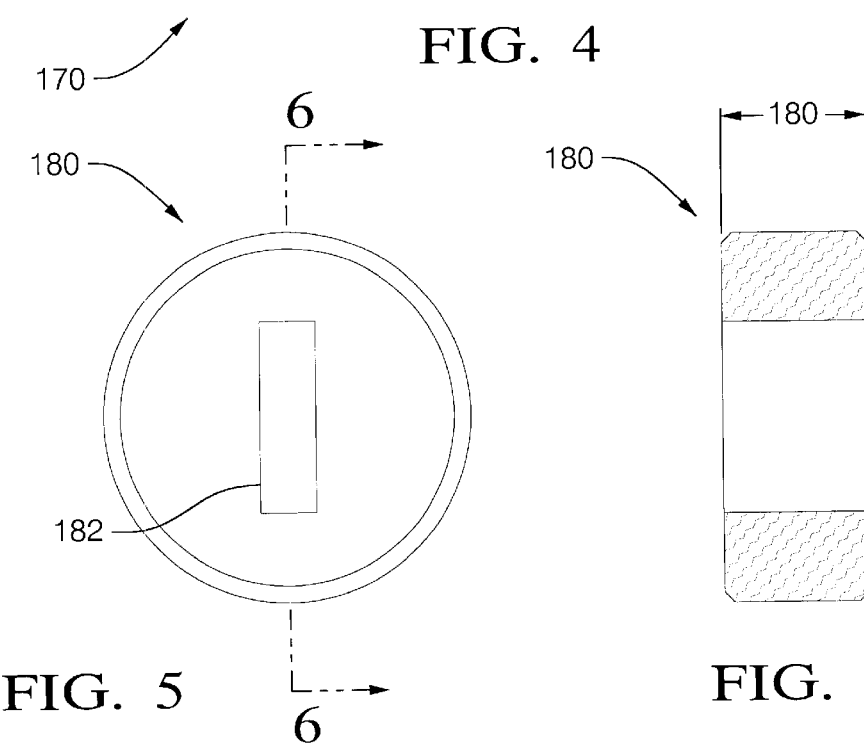
FIG. 5
FIG. 6

METHOD OF PREVENTING MOVEMENT OF A PLANAR SENSOR ELEMENT PACKAGED IN A MAT SUPPORT

TECHNICAL FIELD

The present invention relates generally to exhaust sensors. More particularly, the present invention relates to an improved exhaust sensor and a method of preventing movement of a planar sensor element packaged in a mat.

BACKGROUND OF THE INVENTION

Exhaust Sensors (or exhaust constituent sensors) have been used for many years in automotive vehicles to sense the presence of constituents in exhaust gasses (e.g., oxygen, hydrocarbons, nitrous oxides) and to sense, for example, when an exhaust gas content switches from rich to lean or lean to rich. One known type of exhaust sensor includes a flat plate sensor formed of various layers of ceramic and electrolyte materials laminated and sintered together with electrical circuit and sensor traces placed between the layers in a known manner.

Because automotive exhaust sensors are mounted to members of the vehicle exhaust flow system, the sensors must be durable, be able to withstand vibration and jarring such as would occur during installation and normal vehicle operation, and be able to withstand shock from the occasional stone or other small road debris that may happen to be thrown at the sensor, for example, by the vehicle's tires.

Typically, great care is required when packaging and holding the flat plate sensing element within the outer housing (body) of the exhaust sensor. The flat plate sensing element can be both difficult and expensive to package within the body of the exhaust sensor since it generally has one dimension that is very thin and is usually made of brittle materials. Consequently, great care and time consuming effort must be taken to prevent the flat plate sensing element from being damaged by exhaust, heat, impact, vibration, the environment, etc. This is particularly problematic since most materials conventionally used as sensing element supports, for example, glass and ceramics, typically have a high modulus of elasticity and cannot withstand much bending.

Sensing elements typically have the lower portion of the planar sensor protruding unsupported into the gas stream in a cantilever-type fashion. It is very important to support the portion of the element incident to the element's lower portion properly, else the element will go into resonance and break. However, the element support cannot be too rigid, else it will transmit harmful vibrations to the element. This is a problem with conventional sensors that use ceramic or other rigid supports.

For example, glass seals are commonly used to bond to the element and prevent the element from moving. With glass seals, the planar sensing element is encased and held in proper position within a glass tube, which is itself bonded to a metal shield of the exhaust sensor. Unfortunately, these seals are rigid members that transmit shock pulses to the element. These shock pulses can, and often do, break the element. Glass seals are difficult to install, and they require high temperature cures sustained for long times.

Conventional sensors also are made using ceramic cements as element supports. Ceramic supports are also difficult to install and also have substantially long curing times. Like glass, these supports have a high modulus of elasticity and can transmit shock pulses to the element.

Talc Packs, which are often used as element supports in conventional sensors, are not only rigid enough to transmit shock pulses, but they also require a backing structure into which the talc pack must be compacted to enable compression of the element. The requirement for the backing structure severely limits design choice flexibility.

Accordingly, there remains a need in the art for a durable and rugged exhaust sensor having improved element supports that can be easily manufactured and easily installed.

SUMMARY OF THE INVENTION

The problems and disadvantages of the prior art are overcome and alleviated by the exhaust sensor and method of producing the same, the sensor comprising an elongated planar sensing element having a first end for contacting exhaust gas, a second and opposite end for connecting with at least one electrical terminal, and a central portion extending therebetween; a tubular shield within which at least a portion of said planar sensing element extends; a high temperature mat disposed between said tubular shield and said planar sensing element and about said central portion of said elongated planar sensing element; a shell for mounting said tubular shield to a conduit through which said exhaust gas flows, the shell having a lower shoulder for receiving a lower portion of said tubular shield; and either or both of (1) a disk element support, having an aperture through which at least a portion of said planar sensing element extends, the support disposed between the lower shoulder of said shell and said tubular shield containing the high temperature mat and (2) a vermiculite filled metal mesh support, disposed concentrically around the planar sensing element within the inner wall of the tubular shield.

BRIEF DESCRIPTION OF THE DRAWINGS

The present invention will now be described by way of example with reference to the following Figures, which are meant to be exemplary, not limiting, and in which:

FIG. 3 is an overhead view of an exemplary embodiment of a disk element support as may be used by the sensor of the present invention;

FIG. 4 is a cross-sectional side view of an exemplary embodiment of a disk element support as may be used by the sensor of the present invention;

FIG. 5 is an overhead view of an exemplary embodiment of a metal mesh support as may be used by the sensor of the present invention; and FIG. 6 is a cross-sectional side view of an exemplary embodiment of a metal mesh support as may be used by the sensor of the present invention.

DESCRIPTION OF THE PREFERRED EMBODIMENT

Figure 1:
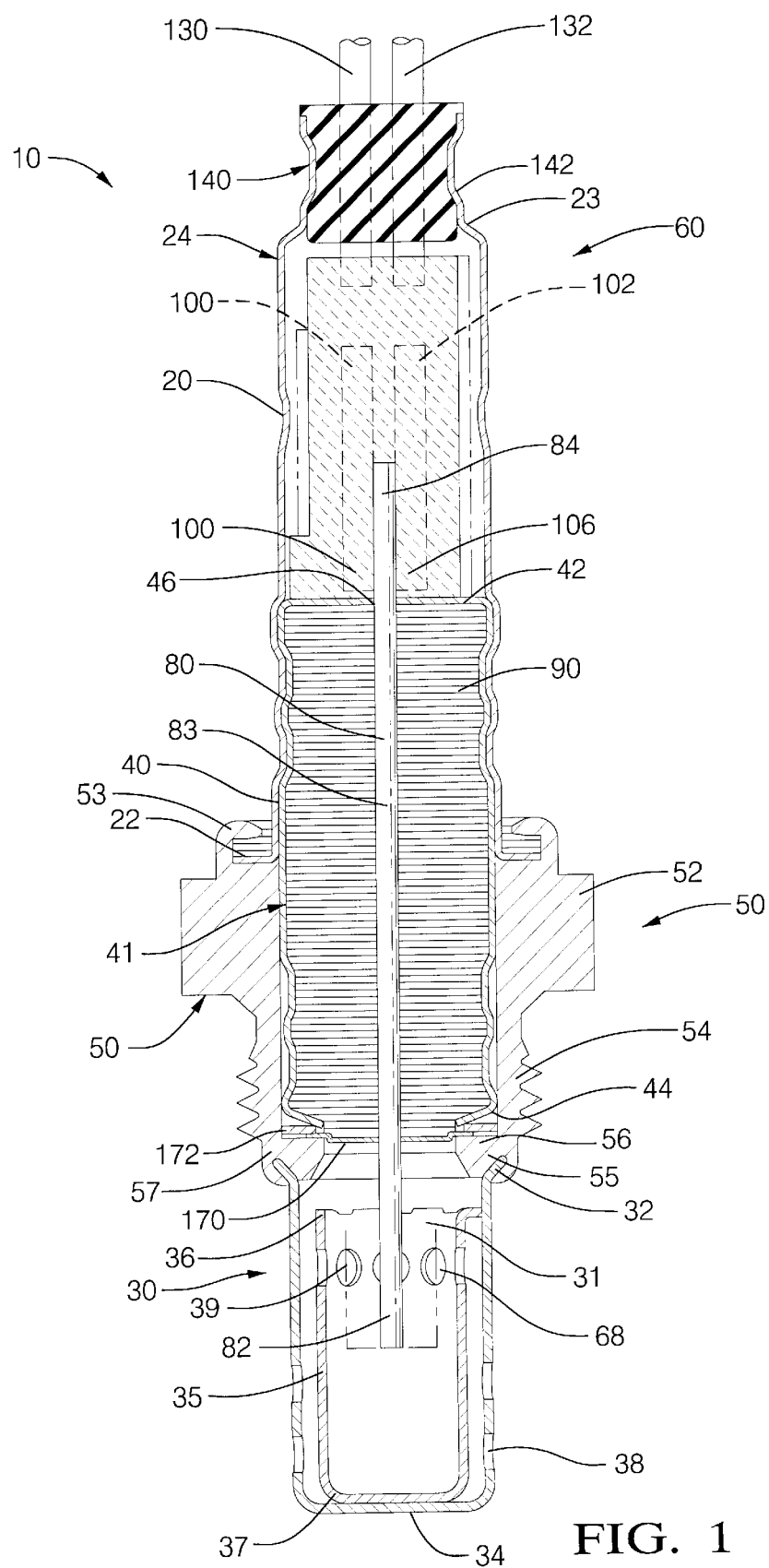
FIG. 1 is a cross-sectional side view of an exemplary embodiment of an exhaust sensor of the present invention incorporating a disk element support.

Referring now to FIG. 1, the example exhaust sensor 10 shown includes a housing structure generally formed of an upper shield 20, a lower shield 30, an inner shield 40 and a shell 50. A terminal connector 60 and a portion of a planar sensing element 80 are disposed within upper shield 20. Planar sensing element 80 is an exhaust sensing element of a known type with any conventional geometry, such as a generally flat elongated rectangular shape. At a first end 82 thereof, planar sensing element 80 includes an exhaust constituent-responsive structure fabricated into planar sensing element 80 in a known manner, preferably along with a heater (not shown) of a known type. At an opposite end 84 of planar sensing element 80, lower ends 104 and 106 of terminals 100 and 102, respectively, contact external pads (not shown) on end 84 to provide electrical connection between terminals 100 and 102 and planar sensing element 80. Ends 104 and 106 of terminals 100 and 102, respectively, are maintained against end 84 of planar sensing element 80 by a compressive force applied by disposing end 84 of planar sensing element 80 between lower ends 104 and 106. Preferably, terminals 100 and 102 comprise spring terminals, the use of which is know in the art and the compressive force generated by disposing end 84 between spring terminals 100 and 102 securely maintains end 84 in electrical contact therewith.

The inner shield 40 has a partially closed first end 42 and a partially closed second end 44 opposite first end 42. A centrally located annular opening 46 is provided at first end 42 and is sized to receive end 84 of planar sensing element 80. Disposed within inner shield 40 are a central portion 83 of planar sensing element 80, and a high temperature mat 90. Optionally, a pair of thermal insulating members (not shown) may be disposed against the planar sensing element 80 for additional support as is known in the art. As used herein, the term "high temperature material" refers to materials that are designed for use in a spark ignition engine environment, where temperatures range from about 300° C. to about 1000° C.

Shell 50 includes a body portion 52 and a threaded portion 54 at a second end 55. Body portion 52 is preferably shaped to accommodate a wrench or other tool for tightening threaded portion 54 into a mount for an exhaust pipe or other component of an exhaust flow system enabling a sensor chamber 31 located within lower shield 30 to be located within a flow of exhaust gasses to be measured. A first end 53 of shell 50 is disposed proximate lower end 22 of the upper shield 20 when shell 50 is securely disposed around inner shield 40 by means known in the art; and preferably, shell 50 is coupled to inner shield 40 by being crimped thereto during the assembly process. Accordingly, shell 50 holds inner shield 40 in compressive force engagement. Formed at second end 55 of shell 50 is a shoulder 56 for contacting partially closed second end 44 of inner shield 40, whereby inner shield 40 rests against shoulder 56 when shell 50 is secured to inner shield 40 during assembly.

In one embodiment of the present invention, high temperature mat 90 extends from closed first end 42 to partially closed second end 44 and extends between planar sensing element 80 and inner surface 41 of inner shield 40. High temperature mat 90 comprises a mat material designed for use in a spark ignition engine environment, whereby high temperature mat 90 is formed of a mat material designed to withstand continuous exposure to temperatures on the order of about 300° C. to about 1000° C. (temperature range observed in spark ignition engine environment). Such materials include ceramic fibrous materials and/or metal mesh, among others. When a ceramic fibrous material is used, the orientation and size of the ceramic fibers are not critical to the practice of the present invention. High temperature mat 90 may be installed in either a preform or fibrous blanket type state around at least a portion of planar sensing element 80 as is known in the relevant arts.

The present invention advocates use of a disk supporting device or a metal mesh support, distinct from the mat material. These supports are capable, individually or in tandem, of securely holding the sensing element in place while at the same time preventing excitation of the sensing element in the weak axis direction. Further, supports used in the present allow the sensing elements to expand freely under elevated thermal conditions, restrict excessive flexing of the elements, and prevent exhaust erosion of sensitive mat materials behind them.

Thus, in the first embodiment of the present invention, shown in FIGS. 1, 3, and 4, disc element support 170 sits between shoulder 56 of the second end 55 of shell 50 and mat 90. The disk element support 170 outer diameter 174 (shown in FIG. 4) is preferably smaller than the inner diameter of the threaded portion 54 of the shell 50. This allows the element to be off-centered and does not put stresses on the element 80. A stabilizing normal force is supplied by the spring action force of partially closed second end 44 of inner shield 40 against the disk element support 170. The normal force, provided by the partially closed second end 44, is opposed by the shoulder 56 of the second end 55 of shell 50. Preferably, washer 172 is provided between the partially closed second end 44 of inner shield 40 and the disk element support 170 to enhance even distribution of the normal force provided by partially closed second end 44.

Disk element support 170 should be made of a material compatible with the environmental conditions of the sensor. Specifically, the disk element support 170 should be capable of maintaining structural integrity in a high temperature environment (up to about 1000° C.). Possible materials include metal, ceramic, composites, and others compatible with the sensor environment.

An aperture 176 should be provided therein, through which the sensing element may be inserted, and preferably, a rectangular slit is made inside the circumference of disk element support 170. This slit can be made in a variety of ways, including cutting, punching, or piercing (shown in FIG. 3) and is preferably made in such a manner that no material is actually removed.

Referring to FIG. 3, width 178 and length 179 correspond generally to the lateral dimensions of the planar sensing element 80. Thus as planar sensing element 80 is forced through aperture 176, the disk material within those dimensions is displaced. When such is the case, the displaced material forms as a support against the sensing element 80, providing a spring action on both long axial sides of the aperture to give maximum protection against vibrations. Further, such displaced support material decreases pressure pulsations from impacting the mat 90 and aids in sealing off exhaust gasses from the mat, which when exposed to such gasses, can erode mat material and cause sensor failure.

The disc material thickness should be thin enough to allow the displaced material, or flaps, to flex without exerting excessive normal force on the element. The thickness of the disc element may be tailored to the particular thickness and strength of the planar element. Suitable material thickness for disk element support 170 is about 0.076 millimeters (0.003 inches) to about 0.508 millimeters (0.020 inches) thick, with about 0.254 millimeters (0.010 inches) to about 0.508 millimeters (0.020 inches) preferred, with about 0.381 millimeters (0.015 inches) particularly preferred.

Where the aperture is instead made substantially to accommodate the dimensions of the planar sensing element (without the preferred slit as described above), the disk element support 170 may have a material thickness substantially greater than 0.508 millimeters (0.020 inches). Indeed, the thickness in this instance is limited only by practical design considerations. Where such is the case, support for the element is provided by the inner surface of the aperture. Accordingly, thicker disk elements provide greater sensor element support.

Figure 2:
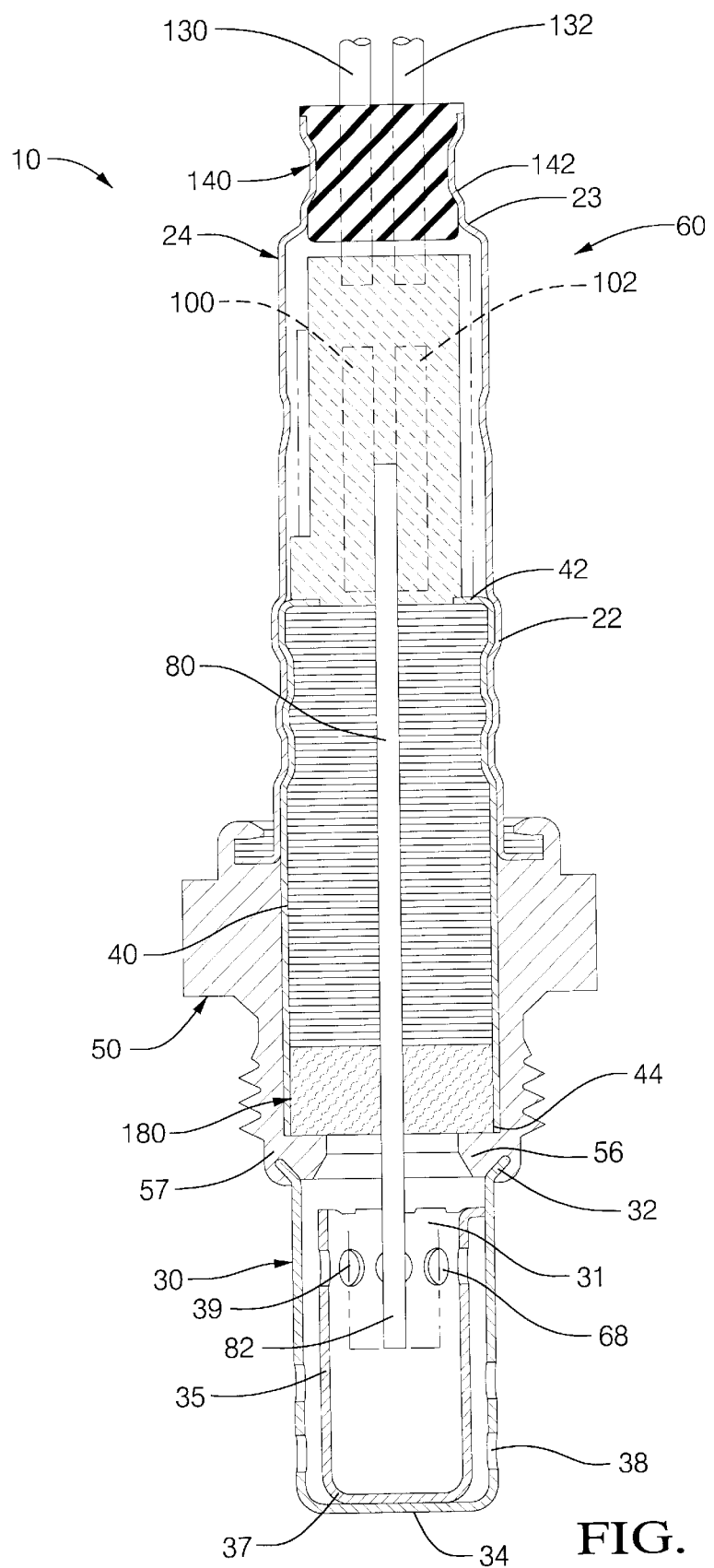
FIG. 2 is a cross-sectional side view of an exemplary embodiment of an exhaust sensor of the present invention incorporating a metal mesh element support.

A particularly preferred embodiment includes a mesh element support 180, shown in FIGS. 2, 5, and 6, used either in conjunction with the disk element support 170 or in lieu of it. The mesh is made from fine wire, impregnated with a filler material to fill the space between the mesh fibers and is compressed into desired form. Any conventional filler is suitable, e.g. clay, however vermiculite filler is preferred due to its ability to expand under elevated temperatures to provide additional sensing element support.

Wire material may be made of any metal, however, metals with high nickel or chrome content are preferred due to their rust resistant properties. Particularly preferred metals include 310, 309, and 316 stainless steels. Suitable thickness for fine wire material used as a mesh element support is from about 0.2 to about 1.2 millimeters, with about 0.4 to about 0.6 millimeters being preferred, and with 0.5 millimeters being particularly preferred. Preferred wire densities are from about 20% to about 50% of the solid density, with the filler material making up the difference, giving a solid density of about 50% to about 70%.

The mesh element support 180 is preferably positioned within inner shield 40 at end 44 of the inner shield 40 and against the disk element support 170 (if present) or shoulder 56 of shell 50. The mesh support provides an aperture 182 for secure support of the planar sensing element 80. The mesh support may replace some or all of the mat material 90, depending on design needs. Use of mesh is particularly preferred due to the increased design flexibility permitted by its use, allowing the proportions of mat material 90, mesh support material 180, use or nonuse of a disk support element 170, and length of the overall sensor to be tailored to particular applications. When used with other support means, the mesh support may or may not be used, depending on design specifications.

The advantages of the preferred mesh element supports lie in the fact that the support prevents element excitation, dampens vibrations, and allows the element to expand due to thermal expansion without inducing stress on the element. Furthermore, mesh elements are easily installed; they do not require talc packs or other supporting structures, and they do not require curing. Further, mesh elements act to diffuse heat across the diameter of the inner surface of the sensor before such heat can damage incident mat materials. This is particularly important in temperature environments up to about 1000° C.

A particular advantage of mesh supports is that as the mesh is installed into the inner shield 40, it is compressed by the walls of the inner shield 40. This compression adds support to the sensing element, securing it against vibrations or impacts. Even greater support is provided once the mesh reaches temperatures above about 300° C., where the vermiculite filler begins to expand, creating a greater compression on the element. Where design considerations call for even greater compression around the element or where installation is insufficient to secure the mesh, crimps (not shown) may be made around the perimeter of the inner shield 40. Also, to aid in assembly of the exhaust sensor, the mesh can be inserted uncompressed into the inner shield 40 and compressed through crimping of the inner shield.

In a preferred configuration for either embodiment, lower shield 30 is securely coupled to shell 50 by engaging flared open end 32 of lower shield 30 with annular recess 57. Shell 50 is itself securely coupled to inner shield 40 by crimping or otherwise affixing shell 50 thereto, whereby first end 82 of planar sensing element 80 is disposed within sensing chamber 31 to permit contact with and sensing of exhaust gas.

Lower shield 30 defines sensing chamber 31 and disposed within lower shield 30 is an internal shield 35 which has an open end 36 for receiving planar sensing element 80 and a closed end 37 adjacent and parallel to closed end 34 of lower shield 30. Lower shield 30 and internal shield 35 incorporate a plurality of apertures 38, 39 for allowing passage of exhaust gas in and out of sensing chamber 31 so that the gasses may be sensed by receptive first end 82 of planar sensing element 80.

The use of terminal connector 60 is known in the art and a suitable terminal connector 60 is also known in the art as an edge card connector or a clam shell connector. Terminal connector 60 typically includes a plurality of electrical terminals with each having a corresponding electrical wire connected thereto. For the purpose of illustration only, sensors 10 and 10' of FIGS. 1 and 2 are shown having a pair of electrical terminals 100 and 102, which are adapted to be connected to electrical wires 130 and 132 in a known manner. Electrical wires 130 and 132 pass through cable seal 140 which generally comprises an elastomeric material suitable for use in a high temperature environment, e.g., spark ignition engine. Cable seal 140 is maintained in place by upper shield 20 which has an upper end 23 forming a seal around a shoulder 142 of cable seal 140, wherein upper shield 20 is crimped in place around cable seal 140 to further secure the same. A central portion 24 of upper shield 20 is disposed around terminal connector 60 and a lower end 22 of upper shield 20 forms a cylindrical opening tightly fit around closed first end 42 of inner shield 40 when sensor 10 is assembled.

For the structures shown in FIGS. 1 and 2, example material for the shields 20, 30, 40, and 35 and for the shell 50 is high chrome or high nickel stainless steel, all steels chosen for high temperature endurance, high-strength and corrosion resistance. Terminal connector 60 may be formed of a thermoplastic or thermoset material (e.g., plastic) or ceramic durable in the high temperature environments to which exhaust sensor 10 is exposed.

Typically, the length of conventional exhaust sensors fall within a limited range because the length had to be such that excessive heat radiating outward from the exhaust system was prevented from contacting the electrical connection at one end of the sensor. However, the sensors of the present invention allow for shortening of overall sensor length should design considerations so require. This is so because each of the disk element support and the metal mesh support effectively diffuse heat away from the mat material and retard erosion of the mat by blocking out exhaust gasses.

An allowed reduction of overall sensor length translates to a reduction in costs and permits the sensor to be mounted in locations which were otherwise inaccessible. This provides greater versatility in positioning and mounting sensors 10 or 10' within the exhaust system.

Finally, incorporation of a disk element support or a metal mesh support effectively provides a product with substantially improved durability and reliability. These supports suppress harmful vibrations which are prevalent in operative environments and add life to the sensor.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An exhaust sensor, comprising:

an elongated planar sensing element having a first end for contacting exhaust gas, a second and opposite end for connecting with at least one electrical terminal, and a central portion extending therebetween;

a tubular shield within which at least a portion of said planar sensing element extends;

a high temperature mat disposed between said tubular shield and said planar sensing element and about said central portion of said elongated planar sensing element;

a shell for mounting said tubular shield to a conduit through which said exhaust gas flows, the shell having a lower shoulder for receiving a lower portion of said tubular shield; and a unitary disk element support, having an aperture adjacent at least a portion of said planar sensing element extending therethrough, the support disposed between the lower shoulder of said shell and said tubular shield containing the high temperature mat.

2. The exhaust sensor as set forth in claim 1, wherein the lower end of said tubular shield is partially closed.

3. The exhaust sensor as set forth in claim 2, further comprising a washer disposed between the partially closed lower end of said tubular shield and said disk element.

4. The exhaust sensor as set forth in claim 1, wherein said disk element support is made of a high temperature material.

5. The exhaust sensor as set forth in claim 1, wherein said disk element support is made of metal or ceramic.

6. The exhaust sensor as set forth in claim 1, wherein the aperture of said disk element support is partially closed, forming flaps, which, when said planar sensing element is inserted, contacts said element.

7. The exhaust sensor as set forth in claim 1, wherein said aperture of said disk element support is a rectangular slit.

8. The exhaust sensor as set forth in claim 5, wherein the material displaced by creation of said rectangular slit forms flaps, which, when said planar sensing element is inserted, contacts said element.

9. The exhaust sensor as set forth in claim 1, wherein the diameter of said disk element support is less than the diameter of the inner wall of said shell at the lower shoulder of said shell.

10. The exhaust sensor as set forth in claim 1, wherein said disk element support is between about 0.076 millimeters (0.003 inches) and 0.508 millimeters (0.020 inches) thick.

11. The exhaust sensor as set forth in claim 1, wherein said disk element support is between about 0.254 millimeters (0.010 inches) and 0.508 millimeters (0.020 inches) thick.

12. A method of preventing movement of a planar sensor element, comprising:

providing an exhaust sensor, comprising:

an elongated planar sensing element having a first end for contacting exhaust gas, a second and opposite end for connecting with at least one electrical terminal, and a central portion extending therebetween;

a tubular shield within which at least a portion of said planar sensing element extends;

a high temperature mat disposed between said tubular shield and said planar sensing element and about said central portion of said elongated planar sensing element;

a shell for mounting said tubular shield to a conduit through which said exhaust gas flows, the shell having a lower shoulder for receiving a lower portion of said tubular shield; and a unitary element support disposed adjacent said elongated planar sensing element at in inner circumference of said element support and disposed adjacent said tubular shield or said shell at an outer circumference of said element support, such support sufficient to dampen vibrations transmitted into said shell and said tubular shield and sufficient to allow for even expansion of said elongated planar sensing element upon exposure to elevated temperatures.

13. The method of claim 12, wherein said element support is a disk element support, said disk element support has an aperture through which at least a portion of said planar sensing element extends.

14. The method of claim 13, wherein the lower end of said tubular shield is partially closed.

15. The method of claim 14, wherein said disk element support is disposed between the lower shoulder of said shell and the lower end of said tubular shield containing the high temperature mat.

16. The method of claim 15, further comprising providing a washer between the partially closed lower end of said tubular shield and said disk element.

17. The method of claim 13, wherein said disk element support is made of a high temperature material.

18. The method of claim 13, wherein said disk element support is made of metal or ceramic.

19. The method of claim 13, wherein the aperture of said disk element support is partially closed, forming flaps, which, when said planar sensing element is inserted, contacts said element.

20. The method of claim 13, wherein the aperture of said disk element support is a rectangular slit.

21. The method of claim 20, wherein the material displaced by creation of said rectangular slit forms flaps, which, when said planar sensing element is inserted, contacts said element.

22. The method of claim 13, wherein the diameter of said disk element support is less than the diameter of the inner wall of said shell at the lower shoulder of said shell.

23. The method of claim 13, wherein said disk element support is between about 0.076 millimeters (0.003 inches) and 0.508 millimeters (0.020 inches) thick.

24. The method of claim 13, wherein said disk element support is between about 0.254 millimeters (0.010 inches) and 0.508 millimeters (0.020 inches) thick.

25. The method of claim 11, wherein said element support is a vermiculite filled metal mesh support, formed as a solid disk, having within the center of the disk an aperture, and having a diameter conforming to that of said tubular shield.

26. The method of claim 25, wherein said metal mesh support is provided in a preform, having an aperture, wherein said support is secured in said tubular shield and said mesh support has an aperture through which said planar sensing element is inserted.

27. The method of claim 25, wherein the metal mesh support is further secured within the tubular shield by crimping the tubular shield thereto.

28. An exhaust sensor, comprising:

an elongated planar sensing element having a first end for contacting exhaust gas, a second and opposite end for connecting with at least one electrical terminal, and a central portion extending therebetween;

a tubular shield within which at least a portion of said planar sensing element extends;

a high temperature mat disposed between said tubular shield and said planar sensing element and about said central portion of said elongated planar sensing element;

a shell for mounting said tubular shield to a conduit through which said exhaust gas flows, the shell having a lower shoulder for receiving a lower portion of said tubular shield; and a unitary vermiculite filled metal mesh support, disposed adjacent to and concentrically around the planar sensing element within and adjacent the inner wall of the tubular shield.

29. The exhaust sensor as set forth in claim 28, wherein the metal mesh support is disposed within the tubular shield and against the lower shoulder of said shell.

30. The exhaust sensor as set forth in claim 28, wherein the metal mesh support is further secured within the tubular shield by crimping the tubular shield thereto.

31. The exhaust sensor as set forth in claim 28, wherein the tubular shield has an upper portion that is partially closed and further comprising a disk element support provided between the high temperature mat and the partially closed upper portion of the tubular shield.

32. The exhaust sensor as set forth in claim 28, further comprising a disk element support provided between said metal mesh support and the lower shoulder of said shell.

33. The exhaust sensor as set forth in claim 28, wherein the metal mesh support is provided in a preform, having an aperture, wherein said support is secured in said tubular shield and said planar sensing element extends through said aperture.

* * * * *